Figure 1:
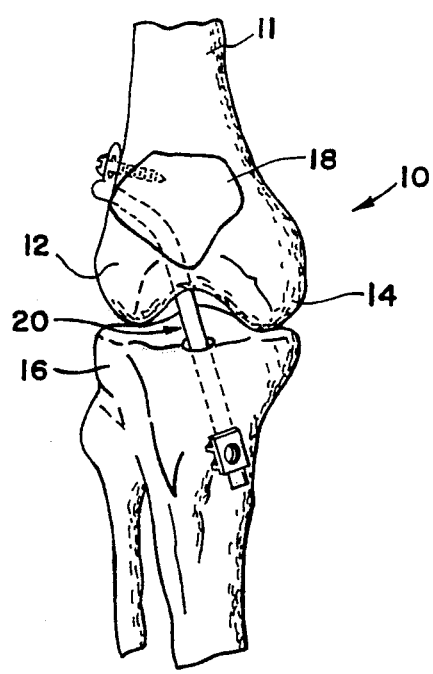

United States Patent [19]

Aikins

[11] Patent Number: 4,917,700
[45] Date of Patent: Apr. 17, 1990

[54] PROSTHETIC LIGAMENT

[75] Inventor: Jerry L. Aikins, Warsaw, Ind.

[73] Assignee: Zimmer, Inc., Warsaw, Ind.

[21] Appl. No.: 226,600

[22] Filed: Aug. 1, 1988

[51] Int. Cl.[4] .............................. A61F 2/08; D04C 1/00
[52] U.S. Cl. ............................................ 623/13; 87/6; 87/7
[58] Field of Search ............................ 623/13; 87/5–8

[56] References Cited

U.S. PATENT DOCUMENTS

| | | | |
|---|---|---|---|
| 3,613,120 | 10/1969 | McFarland, Jr. | 623/13 |
| 4,719,837 | 1/1988 | McConnell et al. | 87/7 X |
| 4,755,183 | 7/1988 | Kenna | 623/13 |

FOREIGN PATENT DOCUMENTS 0249346 12/1987 European Pat. Off. .
2151487 7/1985 United Kingdom ............... 623/13

OTHER PUBLICATIONS

5th International Symposiun—Advances in Cruciate Ligament Reconstruction of the Knee: Prosthetic vs. Autogenous, Mar. 4–6, 1988, Palm Springs, Calif.

Primary Examiner—Alan W. Cannon
Attorney, Agent, or Firm—Paul D. Schoenle

[57] ABSTRACT

A prosthetic ligament includes a braided jacket with an unbraided core which is formed with a portion of the fibers of the braided jacket. This portion is isolated from the remaining braided jacket over a predetermined length of the prosthetic ligament.

4 Claims, 1 Drawing Sheet

U.S. Patent    Apr. 17, 1990    4,917,700

PROSTHETIC LIGAMENT

The present invention covers a prosthetic ligament constructed from a plurality of fibers with a braided jacket and an unbraided core.

In U.S. patent application Ser. No. 07/194,323 filed May 16, 1988, a prosthetic ligament is described with a three-dimensional braid construction. The three-dimensional braid forms an eyelet at one end and a pigtail at the other end. It is possible to secure the eyelet to a femur and utilize the pigtail to extend the prosthetic ligament through a bone tunnel in the femur and tibia. When the prosthetic ligament is stretched to a predetermined tension through the bone tunnel, a staple or the like is driven through the prosthetic ligament into the tibia for tensioned connection to the femur and tibia. The pigtail is then severed from the connected prosthetic ligament.

With a prosthetic ligament implanted between a femur and a tibia, the normal motion of the leg imparts bending and stretching to the prosthetic ligament to maintain the femur juxtaposed the tibia at the knee joint. As a result the femur is properly oriented in alignment with the tibia.

Because of the bending and stretching forces imparted to the prosthetic ligament it is important that the prosthetic ligament be constructed to withstand bending fatigue and elastic deformation.

The present invention teaches a prosthetic ligament with a braided jacket and an unbraided core. The braided jacket accommodates elastic deformation within the limits of the unbraided core. During bending the unbraided core which is disposed within the braided jacket opposes kinking of the braided jacket to reduce regional stresses and extend the fatigue bending life of the prosthetic ligament. The unbraided core substantially fills the lumen formed by the braided jacket so that the inner surfaces of the braided jacket are substantially isolated from each and are thereby protected from abrasion.

It is an advantage of the present invention that the plurality of fibers form the braided jacket and the unbraided core for the prosthetic ligament.

Figure 3:
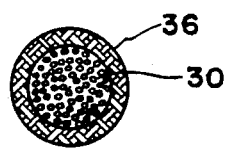
Figure 4:
Figure 2:
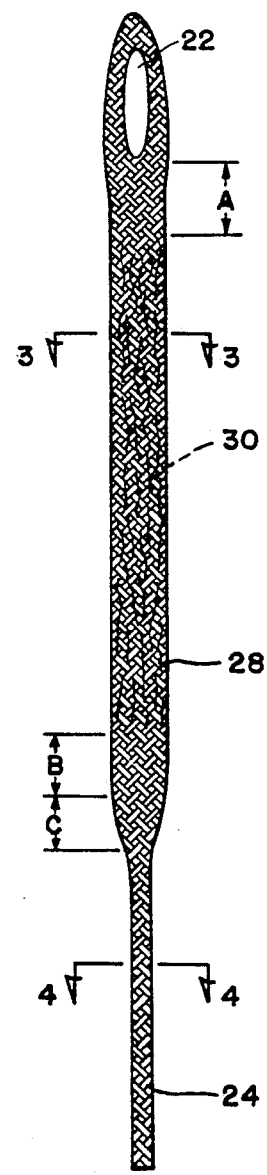
Figure 5:

In the drawings FIG. 1 is a schematic illustration of an anterior cruciate ligament prosthesis extending between a femur and a tibia in a human knee joint. FIG. 2 is a side view of a prosthetic ligament as it exists prior to implantation. FIG. 3 is a cross-sectional view taken along line 3—3 of FIG. 2. FIG. 4 is a cross-sectional view taken along line 4—4 of FIG. 2. FIG. 5 is a view similar to FIG. 2 with a portion of the braided jacket cut away to illustrate the unbraided core.

The human knee joint 10 includes a femur 11 with condyles 12 and 14 adapted for articulation with respect to a tibial plateau 16. A patella 18 helps to orient a patella tendon (not shown). Extending from the lateral side of the distal femur to the medial side of the proximal tibia is a prosthetic ligament 20 constructed in accordance with the present invention and intended to take the place of the natural anterior cruciate ligament which was surgically removed. The prosthetic ligament 20 cooperates with the femur and the tibia to oppose separation between these bones while also permitting articulation and slight extension during normal movement between the femur and tibia.

In FIG. 2 the prosthetic ligament 20 forms an eyelet 22 at one end and a pigtail 24 at the opposite end. The prosthetic ligament is formed with a braided jacket 28. Preferably, the braid construction is a three-dimensional braid, as more fully explained in U.S. patent application Ser. No. 07/194,323, from the eyelet 22 to but not including the pigtail 24. The pigtail braid construction is a two-dimensional braid with a lumen 26, see FIG. 4, defined within the pigtail 24. The main body of the prosthetic ligament includes a core 30 formed by a plurality of fibers extending longitudinally from a first region A to a second region B. In order to form the core, the braiding operation for the eyelet and jacket is interupted at region A so that a plurality of fibers used to form the jacket are separated from the braiding operation but retained in the tow as the core 30. As a result the number of fibers in the three-dimensional braid between regions A and B is less than the number of fibers in the three-dimensional braid at the eyelet end. Therefore, the eyelet end is slightly larger in outer dimension than between region A and B and more pliable in the absence of a core. In region A, the core fibers are gradually separated from the braided jacket so that the core 30 is generated over the length of region A. In a similar manner, the core fibers are gradually reintroduced into the braided jacket 28 in the region B so that all of the fibers are utilized for the three-dimensional braided jacket 28 adjacent a transition zone C where the braided jacket is converted from a three-dimensional braid to a two-dimensional braid.

In a preferred embodiment the eyelet end of the braided jacket 28 is braided first by using a mandrel (not shown) within eyelet 22. A three-dimensional braider with 180 yarns and 118 fibers per yarn commences braiding to form the eyelet 22. At region A, 72 yarns are gradually separated from the braided jacket to form the core 30 with the 72 yarns. The braided jacket 28 between region A and B is braided with 108 yarns (180 yarns—72 yarns), and at region B the 72 yarns are gradually reintroduced into the braided jacket before the transistion zone C. In the transition zone C, 144 yarns are cut out causing a necking down of the outer dimension and leaving 36 yarns to form the pigtail 24 with the lumen 26 in a two-dimensional braid. With the braided ligament as described above, the core 30 acts as a support for the braided jacket 28 to increase bending fatigue resistance between region A and region B, or the substantial length of the prosthetic ligament. Moreover, the core is expeditiously generated from existing fibers in the braided jacket to avoid additional intrusions in the braiding method for constructing the prosthetic ligament.

With the method of construction described above, it is possible to vary the ratio of the number of yarns in the braided jacket to the number of yarns in the unbraided core to either increase or decrease the stiffners of the prosthetic ligament. With more yarn in the unbraided core the stiffners is increased, as contrasted with fewer yarns in the unbraided core resulting in a very pliable prosthetic ligament.

When the prosthetic ligament is implanted between the femur and the tibia, the unbraided core retains the braided jacket in intimate contact with the surface of the bone tunnel so that bone growth into the braided jacket is possible to further secure the prosthetic ligament to the femur and the tibia.

I claim:

1. A prosthetic ligament comprising a plurality of fibers extending between opposite ends, the plurality of fibers forming a braided jacket and an unbraided core, the braided jacket extending over a majority of the length of the prosthetic ligament to surround all of the unbraided core, and the plurality of fibers defining the unbraided core also defining a portion of the braided jacket near at least one end.

2. The prosthetic ligament of claim 1 in which the plurality of fibers defining the unbraided core also define the braided jacket at both ends and the unbraided core defines an intermediate length extending over a substantial length of the prosthetic ligament.

3. The prosthetic ligament of claim 1 in which a transition zone is defined near the one end and a portion of the plurality of fibers form the unbraided core on one side of the transition zone and form a part of the braided jacket on the other side of the transition zone.

4. The prosthetic ligament of claim 3 in which the portion of the plurality of fibers gradually separate from the braided jacket to form the unbraided core at the transition zone while the braided jacket is maintained to surround the unbraided core.

* * * * *